United States Patent [19]

Heather et al.

[11] Patent Number: 4,695,673

[45] Date of Patent: Sep. 22, 1987

[54] PROCESS FOR THE PRODUCTION OF ACYLATED 1,3-DICARBONYL COMPOUNDS

[75] Inventors: James B. Heather, Hercules; Pamela D. Milano, Concord, both of Calif.

[73] Assignee: Stauffer Chemical Company, Westport, Conn.

[21] Appl. No.: 872,069

[22] Filed: Jun. 9, 1986

Related U.S. Application Data

[63] Continuation-in-part of Ser. No. 798,842, Nov. 20, 1985, abandoned, which is a continuation-in-part of Ser. No. 683,882, Dec. 20, 1984, abandoned.

[51] Int. Cl.$^4$ .............................................. C07C 45/54
[52] U.S. Cl. .................................. 568/310; 568/341; 568/346; 568/384; 568/388; 568/314
[58] Field of Search ............... 568/310, 341, 384, 346, 568/388, 314

[56] References Cited

U.S. PATENT DOCUMENTS

| | | | |
|---|---|---|---|
| 3,153,612 | 10/1974 | Molko et al. | 568/314 |
| 4,448,965 | 5/1985 | Henrick | 568/314 |
| 4,482,727 | 11/1985 | Lee | 71/123 |
| 4,545,806 | 10/1985 | John et al. | 71/88 |
| 4,555,263 | 11/1985 | Seiban et al. | 71/98 |
| 4,560,403 | 12/1985 | Motojima et al. | 71/106 |
| 4,584,013 | 4/1986 | Brunner | 71/94 |

FOREIGN PATENT DOCUMENTS

| | | | |
|---|---|---|---|
| 90262 | 10/1983 | European Pat. Off. | 568/346 |
| 2717075 | 10/1978 | Fed. Rep. of Germany | 260/465 D |
| 5113750 | 7/1974 | Japan | 568/310 |
| 784195 | 1/1982 | U.S.S.R. | 568/310 |

OTHER PUBLICATIONS

Akhram et al., Synthesis, pp. 925–927 (1978).
Tanabe et al., Chem. Letters, p. 53 (1952).
Shiori et al., J. Org. Chem., vol. 43, pp. 3631–3632 (1978).
Nogia et al., J. Chem. Soc., Chem. Comm., pp. 459–6 (1985).
Koto et al., Chem. Pharm. Bull., pp. 1679–1682 & 3323–3326 (1984).

*Primary Examiner*—James H. Reamer
*Attorney, Agent, or Firm*—Joel G. Ackerman

[57] ABSTRACT

An acylated 1,3-dicarbonyl compound is produced by rearrangement of the corresponding enol ester in the presence of a cyanide source. In one embodiment the cyanide source is employed with a molar excess of a moderate base, with respect to the enol ester. In another embodiment, the cyanide source is a stoichiometric amount, with respect to the enol ester, of potassium or lithium cyanide and a catalytic amount of a crown ether is used.

49 Claims, No Drawings

PROCESS FOR THE PRODUCTION OF ACYLATED 1,3-DICARBONYL COMPOUNDS

CROSS REFERENCE TO RELATED APPLICATIONS

This application is a continuation-in-part of U.S. Ser. No. 798,842, filed Nov. 20, 1985 now abandoned, which in turn is a continuation-in-part of U.S. application Ser. No. 683,882, filed Dec. 20, 1984 now abandoned.

BACKGROUND AND PRIOR ART

This invention pertains to a process for the production of acylated 1,3-dicarbonyl compounds by rearrangement of corresponding enol esters.

The types of compounds which will be referred to hereinafter as acylated 1,3-dicarbonyl compounds have the general formula

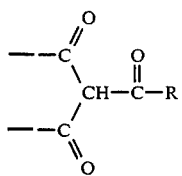

in which R is a group as hereinafter defined (and may generally be an optionally substituted aromatic or aliphatic moiety). Compounds of this type have been described in a number of references as being useful, for instance, as chemical intermediates and/or pesticides. The rest of the molecule, which includes the dicarbonyl group, has a generally cyclical structure.

Most preferably the cyclical 1,3-dicarbonyl group includes a 5- to 6-member ring, which may be carbocyclic or heterocyclic. 6-Membered rings are preferred.

Acylated carbocyclic 1,3-dicarbonyl compounds of this type have the general structure

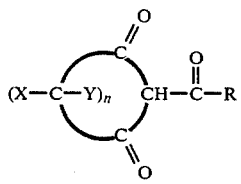

in which R is generally an optionally substituted aliphatic or aromatic moiety as hereinafter defined and n is 2 or 3, preferably 3. The ring may be unsubstituted (all X and Y groups are hydrogen), or one or more hydrogen atoms may be replaced by aliphatic, aromatic, heterocyclic or alkylene groups, preferably hydrocarbyl groups. Examples of such hydrocarbyl groups are alkyl, particularly lower alkyl, phenyl, and $C_2$–$C_5$ alkylene groups such as dimethylene, trimethylene and the like, in which case the compounds have a spiro structure. Examples of other substituents include acyl, carboxyl and carboalkoxy, various substituted phenyl groups and various heterocyclic rings such as pyridyl, pyrimidyl, etc.

This class includes 1,3,5-tricarbonyl compounds; in these compounds two hydrogen atoms bonded to a single carbon atom are replaced by a doubly bonded oxygen atom.

The carbocyclic ring may be saturated or unsaturated, containing an olefinic bond linking the 4- and 5-carbon atoms.

Acylated heterocyclic 1,3-dicarbonyl compounds of this type have the general formula

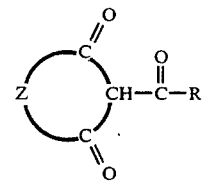

in which R is as defined herein and Z is a chain which contains 2 or 3 ring atoms, at least one of which is nitrogen, oxygen or sulfur. Nitrogen atoms in such rings may be unsubstituted or may be substituted by a $C_1$–$C_4$ alkyl group, preferably a methyl group. Carbon atoms in such rings may be unsubstituted or may be substituted similarly to those in the carbocyclic compounds described above. Where possible, heterocyclic rings may be saturated or unsaturated.

Examples of heterocyclic, 1,3-dicarbonyl structures include, for instance, barbituric acid derivatives, hydroxypyrones, 3,5-dioxotetrahydropyrans and -thiopyrans, cyclical oxolactones, cyclical oxothiolactones and oxolactams.

One method for production of acylated dicarbonyl compounds is disclosed in European Patent Application, Publication No. 90262 and involves the reaction of an optionally substituted 1,3-cyclohexanedione with a substituted benzoyl cyanide. The reaction is carried out in the presence of zinc chloride and triethylamine. Such a process, however, has some drawbacks. Benzoyl cyanides are somewhat expensive reagents, and hydrogen cyanide is produced by this reaction in quantities of about one mole for each mole of acylated dicarbonyl compound. It would be desirable therefore to conduct the reaction using a less expensive and more readily available type of acylating agent which additionally did not produce such quantities of hydrogen cyanide. Benzoyl chlorides, for instance, are a relatively inexpensive and available form of acylating agent. However, benzoyl chlorides are stronger acylating agents than benzoyl cyanides and in the presence of the usual catalysts will tend not to acylate at the carbon atom between the two carbonyl groups, but rather directly attack one of the carbonyl groups itself, forming an enol ester of the type

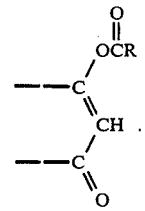

It is known from a number of references that acylated cyclical dicarbonyl compounds may be produced from the corresponding enol esters by rearrangement:

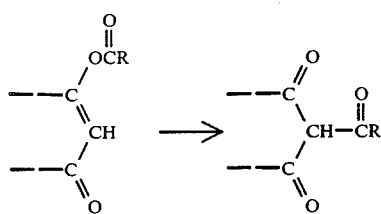
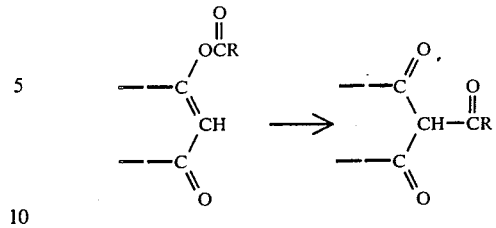

The references disclose several different types of acylated dicarbonyl compounds and various catalysts or promoters for the rearrangement of enol esters to the acylated dicarbonyl compounds.

For instance, Akhrem et al., *Synthesis*, p. 925–927 (1978) disclose the production of a number of acylated cyclohexanediones by reaction of 1,3-cyclohexanedione with an acylating agent (particularly an acyl halide) in two stages. In the first stage the acyl halide is reacted with the cyclohexanedione in the presence of pyridine to produce an enol ester, which is then converted to the acylated cyclohexanedione by rearrangement in the presence of a two-molar excess of aluminum chloride. Acylating agents used in this work had the formula RCOCl in which R was various alkyl (e.g., methyl, ethyl, propyl), phenyl, substituted phenyl, benzyl, and substituted benzyl groups.

Tanabe et al., *Chem. Letters*, p. 53 (1982) describe work on production of 3-acyl-4-hydroxy-2-pyrones by acylation of pyrones with alkyl- or alkenyl-type acyl halides and rearrangement of the enol ester formed using a catalytic amount of 4-dimethylaminopyridine.

European Patent Application (Publication No.) 123001 discloses that other aminopyridine derivatives as well as certain N-alkylimidazole derivatives are suitable catalysts for rearrangement of enol esters to acylated cyclohexanediones having a 5-carboxylate substituent.

USSR. Pat. No. 784,195 discloses rearrangement of an enol ester to produce 2-oleoyl-cyclohexane-1,3-dione in the presence of molten sodium acetate at 160°–170° C. European Patent Application, Publication No. 80301 discloses rearrangement of enol esters of 5-(polymethylphenyl)-1,3-cyclohexanediones to the corresponding acylated cyclohexanediones in the presence of a Lewis acid. Acylating agents used included anhydrides and acyl halides of the formula RCOCl in which R was alkyl, fluoroalkyl, alkenyl, alkynyl, or phenyl.

SUMMARY OF THE INVENTION

This invention pertains to a process for producing an acylated cyclical 1,3-dicarbonyl compound by rearrangement of the corresponding enol ester in which the rearrangement is conducted in the presence of a cyanide source.

This invention also includes certain novel enol esters.

DETAILED DESCRIPTION OF THE INVENTION

This invention concerns a process for producing an acylated cyclical 1,3-dicarbonyl compound by rearrangement of an enol ester according to the general reaction in which the rearrangement is conducted in the presence of a cyanide source. As can be seen from the above formula, the enol esters are esters of carboxylic acids and the term "enol ester" as used herein refers to esters of carboxylic acids.

More particularly, the rearrangement is conducted in the presence of either
(a) a catalytic amount of a cyanide source and a molar excess, with respect to the enol ester, of a moderate base, for instance, a trialkylamine, an alkali metal carbonate or an alkali metal phosphate; or
(b) a stoichiometric amount, with respect to the enol ester, of potassium cyanide or lithium cyanide, and a catalytic amount of a cyclical crown ether or an acyclic analog thereof.

The products of this reaction have the general formula

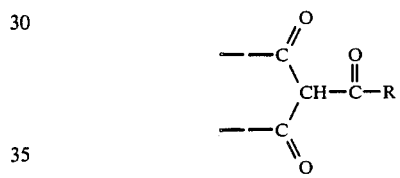

in which R may be variously alkyl, alkenyl, aryl (e.g., phenyl or substituted phenyl), phenalkyl (e.g. optionally substituted benzyl, phenethyl, etc.), or other groups, for instance those mentioned in the references described above.

The remainder of the molecule includes a chain of atoms linking the carbon atoms of the two carbonyl groups to form a cyclic compound. This chain contains two or three atoms and may be composed totally of carbon atoms (the ring is a carbocyclic ring) or may contain one or more nitrogen, sulfur or oxygen atoms (the ring is a heterocyclic ring). Preferably the ring contains a total of six atoms.

Acylated carbocyclic 1,3-dicarbonyl compounds of this type have the general formula

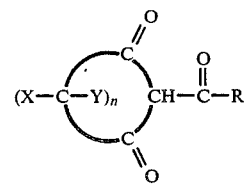

in which R is generally an optionally substituted aliphatic or aromatic moiety as hereinafter defined and n is 2 or 3, preferably 3. The ring may be unsubstituted (all X and Y groups are hydrogen), or one or more hydrogen atoms may be replaced by aliphatic, aromatic, heterocyclic or alkylene groups, preferably hydrocarbyl groups. Examples of such hydrocarbyl groups are alkyl, particularly lower alkyl, phenyl, and $C_2$-$C_5$ alkylene groups such as dimethylene, trimethylene and the like, in which case the compounds have a spiro structure. Examples of other substituents include acyl, carboxyl and carboalkoxy, various substituted phenyl groups and various heterocyclic rings such as pyridyl, pyrimidyl, etc.

This class includes 1,3,5-tricarbonyl compounds; in these compounds two hydrogen atoms bonded to a single carbon atom are replaced by a doubly bonded oxygen atom and one ring carbon is disubstituted.

The carbocyclic ring may be saturated or unsaturated, containing an olefinic bond linking the 4- and 5-carbon atoms.

Acylated heterocyclic 1,3-dicarbonyl compounds of this type have the general formula $$\underset{Z}{\overset{}{\bigcirc}}\begin{matrix}\overset{O}{\underset{\|}{C}}\\ CH-\overset{O}{\underset{\|}{C}}-R\\ \underset{\|}{C}\\ O\end{matrix}$$

in which R is as defined herein and Z is a chain which contains 2 or 3 ring atoms, at least one of which is nitrogen, oxygen or sulfur. Nitrogen atoms in such rings may be unsubstituted or may be substituted by a $C_1$-$C_4$ alkyl group, preferabky a methyl group. Carbon atoms in such rings may be unsubstituted or may be substituted similarly to those in the carbocyclic compounds described above. Where possible, heterocyclic rings may be saturated or unsaturated.

Examples of heterocyclic 1,3-dicarbonyl structures include, for instance, barbituric acid derivatives, hydroxypyrones, 3,5-dioxotetrahydropyrans and -thiopyrans, cyclical oxolactones, cyclical oxothiolactones and oxolactams.

One preferred class of products is that in which the dicarbonyl compound is an optionally substituted cyclohexanedione and the acylating group is a substituted benzoyl moiety. That is, R is substituted phenyl. In general, these compounds have the formula in which
$R^1$, $R^2$, $R^3$, $R^4$, $R^5$ and $R^6$ are independently hydrogen or $C_1$-$C_6$ alkyl (preferably $C_1$-$C_4$ alkyl) or $R^1$ or $R^3$ is $$R_aO\overset{O}{\underset{\|}{C}}-$$

in which $R_a$ is $C_1$-$C_4$ alkyl; phenyl, optionally substituted by from 2 to 5 methyl groups;
or in which $R^1$ and $R^2$, or $R^3$ and $R^4$, taken together are $C_2$-$C_5$ alkylene (such compounds have a spiro structure);
$R^7$ is halogen (chlorine, bromine, iodine or fluorine); cyano; $C_1$-$C_4$ alkyl; $C_1$-$C_4$ haloalkyl (preferably trifluoromethyl); $R_kS$ in which $R_k$ is $C_1$-$C_4$ alkyl; $C_1$-$C_4$ alkoxy (preferably methoxy) or nitro;

$R^8$, $R^9$ and $R^{10}$ independently are hydrogen or substituents including halogen; $C_1$-$C_4$ alkyl; $C_1$-$C_4$ alkoxy, trifluoromethoxy; cyano; nitro; $C_1$-$C_4$ haloalkyl; $C_1$-$C_4$ alkylthio; phenoxy; or substituted phenoxy in which the substituent is halogen or halomethyl or both;

$R_bS(O)n$ in which n is 0, 1 or 2; and $R_b$ is $C_1$-$C_4$ alkyl, $C_1$-$C_4$ haloalkyl, phenyl or benzyl, $$R_c\overset{O}{\underset{\|}{C}}NH-$$

in which $R_c$ is $C_1$-$C_4$ alkyl,

—$NR_dR_e$ in which $R_d$ and $R_e$ independently are hydrogen or $C_1$-$C_4$ alkyl;

$R_fC(O)$— in which $R_f$ is hydrogen, $C_1$-$C_4$ alkyl, $C_1$-$C_4$ haloalkyl or $C_1$-$C_4$ alkoxy;

$SO_2NR_gR_h$ in which $R_g$ and $R_h$ independently are hydrogen or $C_1$-$C_4$ alkyl;

or $R^8$ and $R^9$ taken together form a ring structure with two adjacent carbon atoms of the phenyl ring to which they are attached.

Compounds of this type, with various substituents on either or both of the cyclohexane or phenyl rings are disclosed in: European Patent Application, Publication No. 90262; the following copending United States patent applications, all of William J. Michaely et al., assigned to the Assignee herewith, and entitled "Certain 2-(2-Substituted Benzoyl)-1,3-Cyclohexanediones:" Ser. No. 634,408, filed July 31, 1984; Ser. No. 640,791, filed Aug. 17, 1984; Ser. No. 752,702, filed July 8, 1985; and Ser. No. 722,593, filed Sept. 5, 1985; the following U.S. patent applications assigned to the Assignee hereof, Ser. No. 683,900, filed Dec. 20, 1984 and Ser. No. 802,135, filed Nov. 29, 1985, entitled "Certain 2-(2-Nitrobenzoyl)-1,3-Cyclohexanediones", of Charles G. Carter; Ser. No. 683,899, filed Dec. 20, 1984, entitled "Certain 2-(2'-Cyanobenzoyl)-1,3-Cyclohexanediones", of Charles G. Carter; Ser. No. 683,898, filed Dec. 20, 1984 and Ser. No. 802,133, filed Nov. 29, 1985, entitled "Certain 2-(2'Substituted Benzoyl)-1,3-Cyclohexanediones", of Charles G. Carter et al.; Ser. No. 683,884, filed Dec. 20, 1984 and Ser. No. 802,134, filed Nov. 29, 1985, entitled "Certain 2-(2'-Alkylbenzoyl)-1,3-Cyclohexanediones", of Charles G. Carter (all these patent applications relating to compounds which are herbicidal) and Japanese Patent Applications (Publication Nos.) 51/13750 and 51/13755 of Nippon Soda K.K., which disclose some compounds of this type as intermediates for herbicides. The disclosures of these documents are hereby incorporated herein.

This invention also includes the enol esters of such compounds in which $R^7$ is halogen. Such enol esters have the formula

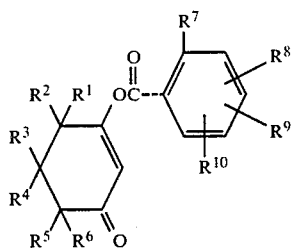

in which $R^7$ is halogen and $R^1$, $R^2$, $R^3$, $R^4$, $R^5$, $R^6$, $R^8$, $R^9$ and $R^{10}$ are as defined above.

Preferably, $R^1$, $R^2$, $R^5$ and $R^6$ are hydrogen; $R^3$ and $R^4$ are independently hydrogen or $C_1$–$C_4$ alkyl; or $R^3$ is

in which $R_a$ is $C_1$–$C_4$ alkyl, $R^7$ is halogen or $C_1$–$C_4$ alkoxy and $R^8$, $R^9$ and $R^{10}$ are as defined above. Most preferably, $R^1$–$R^6$ are all hydrogen.

Examples of such compounds are those in which $R^1$–$R^6$ are all hydrogen and;

$R^7$ is chloro, $R^8$ is 3-chloro, $R^9$ is 4-chloro and $R^{10}$ is hydrogen;

$R^7$ is chloro, $R^8$ is hydrogen, $R^9$ is 4-methylsulfonyl and $R^{10}$ is hydrogen;

$R^7$ is chloro, $R^8$ is 3-ethoxy, $R^9$ is 4-ethylsulfonyl and $R^{10}$ is hydrogen;

$R^7$ is chloro, $R^8$ is 3-methoxy, $R^9$ is 4-ethylthio and $R^{10}$ is hydrogen;

$R^7$ is chloro, $R^8$ is 3-(n-butoxy), $R^9$ is 4-ethylsulfonyl and $R^{10}$ is hydrogen; and $R^7$ is chloro, $R^8$ is 3-methylcarbamyl, $R^9$ is 4-chloro and $R^{10}$ is hydrogen.

Another preferred class of products is that in which the 1,3-dicarbonyl compound is a 1,3,5-cyclohexanetrione and the acylating group is a substitured benzoyl moiety. Compounds of this type are disclosed in copending, commonly assigned U.S. patent application Ser. No. 872,061, filed concurrently herewith, of Charles G. Carter, entitled "Certain 2-Benzoyl-1,3,5-cyclohexanetriones" and have the general formula

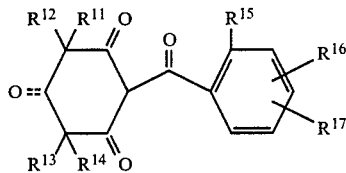

wherein
$R^{11}$ is hydrogen or $C_1$–$C_4$ alkyl, preferably methyl;
$R^{12}$ is hydrogen or $C_1$–$C_4$ alkyl, preferably methyl; or
$R^{11}$ and $R^{12}$ together are $C_2$–$C_5$ alkylene;
$R^{13}$ is hydrogen or $C_1$–$C_4$ alkyl, preferably methyl;
$R^{14}$ is hydrogen or $C_1$–$C_4$ alkyl, preferably methyl; or
$R^{13}$ and $R^{14}$ together are $C_2$–$C_5$ alkylene;
$R^{15}$ is hydrogen; halogen; $C_1$–$C_2$ alkyl, preferably methyl; $C_1$–$C_2$ alkoxy, preferably methoxy; nitro; cyano; $C_1$–$C_2$ haloalkyl, preferably trifluoromethyl; or $R^mS$– wherein $R^m$ is $C_1$–$C_2$ alkyl, preferably methyl, trifluoromethyl or difluoromethyl; or trifluoromethoxy or difluoromethoxy. Preferably, $R^{15}$ is chlorine, bromine, $C_1$–$C_2$ alkyl, $C_1$–$C_2$ alkoxy, trifluoromethyl, cyano, nitro, $C_1$–$C_2$ alkylthio or $C_1$–$C_2$ alkylsulfonyl; more preferably chlorine, nitro, methyl, trifluoromethyl or methylsulfonyl; and $R^{16}$ and $R^{17}$ independently are (1) hydrogen; (2) halogen, preferably chlorine, fluorine or bromine; (3) $C_1$–$C_4$ alkyl, preferably methyl; (4) $C_1$–$C_4$ alkoxy, preferably methoxy; (5) trifluoromethoxy; (6) cyano; (7) nitro; (8) $C_1$–$C_4$ haloalkyl, more preferably trifluoromethyl; (9) $R^bSO_n$– wherein n is the integer 0, 1 or 2, preferably 2; and $R^b$ is (a) $C_1$–$C_4$ alkyl, preferably methyl;
(B) $C_1$–$C_4$ alkyl substituted with halogen or cyano, preferably chloromethyl, trifluoromethyl or cyanomethyl;
(c) phenyl; or
(d) benzyl;

(10) —$NR^dR^e$ wherein
$R^d$ and $R^e$ independently are hydrogen or $C_1$–$C_4$ alkyl;

(11) $R^fC(O)$— wherein $R^f$ is $C_1$–$C_4$ alkyl or $C_1$–$C_4$ alkoxy;

(12) —$SO_2NR^dR^e$ wherein $R^d$ and $R^e$ are as defined; or

(13) —$N(R^d)C(O)R^e$ wherein $R^d$ and $R^e$ are as defined.

The disclosure of this patent application is hereby incorporated herein.

A third class of products is that in which the 1,3-dicarbonyl compound includes a heterocylic ring, as defined above.

Some more specific types of such compounds include:

Hydroxypyrones, such as those described in Tanabe et al., supra and in U.S. Pat. No. 4,482,727;

barbituric acid derivatives such as those of the formula

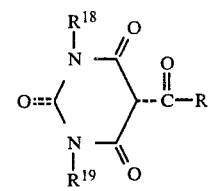

in which $R^{18}$ and $R^{19}$ are hydrogen or $C_1$–$C_4$ alkyl (preferably methyl) and R is substituted phenyl such as

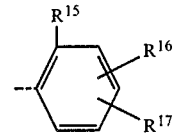

in which $R^{15}$, $R^{16}$ and $R^{17}$ are as defined above. Such compounds are described, for instance, in copending, commonly assigned United States patent application Ser. No. 872,068, filed concurrently herewith, of David L. Lee and Charles G. Carter, entitled "Certain S-(2-Substituted Benzoyl)-Barbituric Acids, the disclosure of which is hereby incorporated herein; and in U.S. Pat. No. 3,999,974 (R is halo-substituted phenyl);

oxolactams such as those having the formula

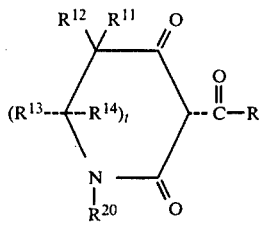

in which $R^{11}$–$R^{14}$ and $R^{20}$ are independently hydrogen or $C_1$–$C_4$ alkyl, or $R^{11}$ and $R^{12}$ together are $C_2$–$C_5$ alkylene, t is 0 or 1 and R is substituted phenyl such as

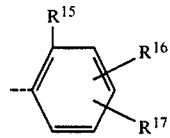

in which $R^{15}$–$R^{17}$ are as previously defined. Such compounds are disclosed, for instance, in copending, commonly assigned U.S. application Ser. No. 871,973, now abandoned, continuation-in-part 021,811 filed 3/13/87, filed concurrently herewith, of Jeffrey K. Curtis, entitled "Certain 3-Benzoyl-4-Oxolactams, the disclosure of which is hereby incorporated herewith;

certain oxolactones and oxothiolactones such as those having the formula

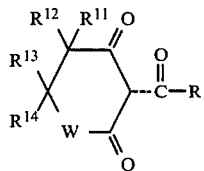

in which $R^{11}$–$R^{14}$ are independently hydrogen or $C_1$–$C_4$ alkyl; or $R_{11}$ and $R^{12}$ together are $C_2$–$C_5$ alkylene; or $R^{13}$ and $R^{14}$ together are $C_2$–$C_5$ alkylene; or $R^{11}$ and $R^{13}$ together form a bond, and R is substituted phenyl such as

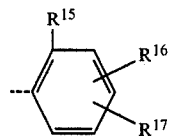

in which $R^{15}$–$R^{17}$ are as defined above; and W is oxygen or sulfur. When $R_{11}$ and $R_{13}$ together form a bond, the compounds contain an unsaturated heterocyclic ring. Such compounds are disclosed, for instance, in co-pending, commonly assigned U.S. application Ser. No. 811,975, filed concurrently herewith, of Donald R. James, Christopher Knudsen, William J. Michaely and Hsaio-Ling Chin, entitled "Certain 4-Oxo-Benzoyl-Valerolactones and Thiolactones", the disclosure of which is hereby incorporated herein. (Additional compounds are disclosed in European Patent Application (publication No.) 40,082);

dioxotetrahydropyrans and -thiopyrans such as those having the formula

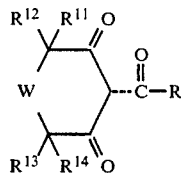

in which $R^{11}$–$R^{14}$ are independently hydrogen or $C_1$–$C_4$ alkyl or $R^{11}$ and $R^{12}$ together are $C_2$–$C_5$ alkylene, or $R^{13}$ and $R^{14}$ together are $C_2$–$C_5$ alkyene; W is oxygen or sulfur and R is substituted phenyl such as

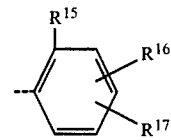

in which $R^{15}$–$R^{17}$ are as previously defined. Such compounds are described, for instance, in copending, commonly assigned U.S. application Ser. No. 872,080, of Jeffrey K. Curtis and Charles G. Carter, entitled "Certain Substituted 4-Benzoyl-3,5-Oxotetrahydropyrans and Thiopyrans", the disclosure of which is incorporated herein.

Additional compounds are disclosed, for instance, in U.S. application Ser. No. 871,974, commonly assigned, filed concurrently herewith, of Charles G. Carter, entitled "Certain 2-Phenylacetyl-1,3,5-Cyclohexanetriones", the disclosure of which is hereby incorporated herein.

Some other compounds to which this process may be applied are disclosed in copending United States patent applications (commonly assigned) Ser. No. 764,110, filed Aug. 26, 1985 of David L. Lee et al., entitled "Certain 2-(2-Substituted Phenylacetyl)-1,3-Cyclohexanediones, now European patent Application Publication No. 162,336; and Ser. Nos. 683,883, filed Dec. 20, 1984 and 804,207, filed Dec. 3, 1985, of David L. Lee et al., entitled "Certain 2-(2'-Substituted Benzoyl)-1,3-Cyclopentanediones," and compounds disclosed in literature mentioned under the heading "Background and Prior Art."

The rearrangement process of this invention is carried out in the presence of a cyanide source. The term "cyanide source" refers to a substance or substances which under the rearrangement conditions consists of or generates hydrogen cyanide and/or cyanide anion. There are two primary embodiments.

In one embodiment, the process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; benzaldehyde cyanohydrin; cyanohydrins of $C_2$–$C_5$ aliphatic aldehydes such as acetaldehyde cyanohydrin, propionaldehyde cyanohydrin, etc.; cyclohexanone cyanohydrin; lactonitrile; lower alkyl silyl cyanides, notably di- and tri-(lower alkyl)silyl cyanides such as dimethyl- and trimethyl-silyl cyanides; potassium ferricyanide; and hydrogen cyanide itself.

Hydrogen cyanide is considered most advantageous as it produces relatively rapid reaction and is inexpensive. It may be used in either liquid or gaseous form; it may be purchased from a commercial supplier or generated on-site by reaction of a metal cyanide with an acid. Among cyanohydrins the preferred cyanide source is acetone cyanohydrin.

In this embodiment, the cyanide source is used in an amount up to about 50 mole percent based on the enol ester. It may be used in as little as about 1 mole percent to produce an acceptable rate of reaction at about 40° C. on a small scale. Larger scale reactions give more reproducible results with slightly higher catalyst levels of about 2 mole percent. Generally about 1–10 mole % of the cyanide source is preferred.

In this embodiment the process is conducted with a molar excess, with respect to the enol ester, of a moderate base. By the term "moderate base" is meant a substance which acts as a base yet whose strength of activity as a base lies between that of strong bases such as hydroxides (which could cause hydrolysis of the enol ester) and that of weak bases such as N,N-dimethylaniline (which would not function effectively). Moderate bases suitable for use in this embodiment include both organic bases such as trialkylamines and inorganic bases such as alkali metal carbonates and phosphates. The trialkylamines are preferably tri(lower alkyl)amines having from 1 to 6, preferably 1 to 4 carbon atoms per alkyl group. A particularly preferable amine is triethylamine. Suitable inorganic bases include potassium carbonate and trisodium phosphate. Even a bicarbonate such as potassium bicarbonate will function effectively in this reaction when used in combination with a dipolar aprotic solvent such as dimethylformamide.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed, depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures from about 0° C. up to about 100° C. Preferably the temperature is at a maximum of about 80° C. Most preferably the temperature is from about 20° C. to about 50° C. In some cases, for instance when there is a possible problem of excessive by-product formation (for instance, when using an ortho-cyano benzoyl halide) the temperature should be kept at about 40° C. maximum.

In the second primary embodiment of this process, potassium or lithium cyanide serves as the cyanide source, but is used in a stoichiometric amount with respect to the enol ester, without using a separate base. The cyanide source is employed together with a catalytic amount of a phase transfer catalyst which is a crown ether or an acyclic analog thereof.

The preferred cyanide source is this embodiment is potassium cyanide. The preferred crown ether for this source is 18-crown-6. Other hexadentate compounds such as cyclohexyl-18-crown-6, dibenzo-18-crown-6, and the acyclic compound pentaethylene glycol dimethyl ether, would also be suitable.

For lithium cyanide, 15-crown-5 is suitable.

In this embodiment, a portion of the potassium or lithium cyanide serves as the base so that a separate base is not necessary.

This embodiment is suitable for production of compounds of the general type, but has been found particularly satisfactory for use where milder conditions are advantageous or necessary to minimize by-product formation, such as in the preparation of benzoylated cyclohexanediones having an ortho-cyano substituent on the phenyl ring. This embodiment of the process can be carried out at room temperature. Solvents similar to the first embodiment may be employed; acetonitrile is preferred.

The process according to either embodiment may be carried out using the enol ester as the starting material, or with generation of the enol ester in situ, for instance by reaction of an acylating agent with a diketone.

When the enol ester is utilized as a starting material in either embodiment of the process, it may be prepared by any of a number of known means, including acylation of a dicarbonyl compound with, for instance, an acyl halide.

The production of acylated dicarbonyl compounds according to this invention, starting with acylating agents and dicarbonyl compounds (for example, acyl halides such as substituted benzoyl halides and dicarbonyl compounds such as cyclohexanediones) may be be advantageously carried out with or without isolation of the intermediate enol ester. When carried out in two steps, the acyl halide or other acylating agent and the dicarbonyl compound are reacted in the presence of a moderate base such as triethylamine. The enol ester may be isolated from the resulting product isolated from the resulting product mix by known techniques, for instance washing the resultant solution with acid and base, and with saturated sodium chloride solution, and drying. Such a technique is advantageous when a different solvent is preferred for the second step—the rearrangement of the enol ester to the acylated dicarbonyl compound. The dried enol ester may be mixed with an appropriate solvent such as acetonitrile or 1,2-dichloroethane, and contacted with the appropriate amounts of cyanide source and either moderate base or Crown ether, according to which embodiment is used, at an appropriate temperature, to produce the final product.

Alternatively, the enol ester may be retained in the reaction product and the second stage may be carried out (using the same solvent) by adding a cyanide source and additional base if necessary (in that embodiment), to produce the acylated dicarbonyl compound.

In another process variation, the acylated dicarbonyl compound may be obtained in one step via the in situ formation and rearrangement of the enol ester by reacting the acyl halide or other acylating agent with the dicarbonyl compound in the presence of an appropriate amount of cyanide source and a suitable amount of a moderate base or crown ether, according to which embodiment is used.

Comparable yields can be obtained either with or without isolation of the enol ester.

The acylated dicarbonyl compound is obtained from this reaction in the form of its salt. The desired acylated dicarbonyl compound may be obtained by acidification and extraction with an appropriate solvent, if necessary.

The conduct of the process of this invention is illustrated by the following examples.

EXAMPLE 1

Rearrangement of Enol Ester

A series of experiments was carried out on the production of 2-(2',3',4'-trichlorobenzoyl)-1,3-cyclohexanedione by rearrangement of its enol ester utilizing various cyanide sources and solvents. The general procedure was as follows: 3.0 grams (g) (0.0094 mole) of the enol ester (prepared by reaction of 2,3,4-trichlorobenzoyl chloride with 1,3-cyclohexanedione in the presence of triethylamine, and isolated) was dissolved in 10 milliliters (ml) of the indicated solvent and 10 mole percent of the indicated catalyst and 140 mole percent of triethylamine (both quantities with respect to the enol ester) were added. The mixture was maintained at ambient temperature and reaction was allowed to proceed for 4–18 hours. The reaction mixture was diluted with water and the solvent was removed by distillation under reduced pressure. The resulting aqueous mixture was acidified to a pH of about 1 by the slow addition of 6N hydrochloric acid, with stirring. The resulting solids were collected by filtration and dried to constant weight at 75° C.

The yield of the crude acylated dicarbonyl compound, uncorrected for purity of the starting materials, is given below in Table 1.

TABLE 1

| Catalyst | Solvent | Theoretical Yield, % | Product Purity, % |
|---|---|---|---|
| KCN | acetonitrile | 91.3 | 82.8 |
| KCN | acetonitrile | 91.0 | 81.9 |
| KCN | acetonitrile | 95.3 | 84.6 |
| KCN | 1,2-dichloroethane | 87.3 | 76.0 |
| KCN | 90% 1,2-dichloroethane/ 10% dimethylformamide | 86.0 | 75.7 |
| NaCN | 1,2-dichloroethane | 78.7 | 80.3 |
| acetone cyanohydrin | acetonitrile | 92.0 | 80.1 |

EXAMPLE 2

Preparation of Acylated Dicarbonyl Compound Without Isolation of Enol Ester

This example illustrates the process starting from an acyl halide and a dicarbonyl compound, in one step, without isolation of the intermediate enol ester. The procedure was as follows:

There were placed in flask 3.0 g (0.027 mole) 1,3-cyclohexanedione, 15 ml of 1,2-dichloroethane and 10 mole percent (with respect to the intermediate enol ester) of sodium cyanide. The reaction mixture was blanketed with nitrogen and maintained at about room temperature. Then, 300 mole percent triethylamine (based on the enol ester) was added, with the mixture still being kept at room temperature. Then, 100 mole percent (with respect to the dione) of 2,3,4-trichlorobenzoyl chloride was added to the mixture. The mixture was maintained at ambient temperature and reaction was allowed to proceed for about 24 hours. The product was recovered as in Example 1, yielding 8.04 g of crude product (93.2% of theoretical, uncorrected for purity of the starting materials).

EXAMPLES 3–6

A series of experiments was conducted similar to that described in Example 2, but using different catalysts and solvents. The same reactants were employed. All catalysts wer used in an amount of 10 mole %, based on the intermediate enol ester. Table 2 contains the results of these experiments, with the yields being uncorrected for purity of the starting materials.

TABLE 2

| Ex. No. | Catalyst | Solvent | Theoretical Yield, % | Product Purity, % |
|---|---|---|---|---|
| 3 | KCN | methylene chloride | 81.1 | 80.5 |
| 4 | KCN | 1,2-dichloroethane | 87.5 | 69.9 |
| 5 | acetone cyanohydrin | 1,2-dichloroethane | 90.7 | 82.6 |
| 6 | acetone cyanohydrin | toluene | 90.4 | 79.3 |

EXAMPLE 7

This example also represents the conduct of the process without isolation of the intermediate enol ester.

In a flask there were placed 15 grams (0.13 mole) 1,3-cyclohexanedione, 75 ml 1,2-dichloroethane and 0.24 ml (2 mole percent based on the enol ester) acetone cyanohydrin. The materials were placed under a nitrogen blanket and the flask placed in an ice bath.

Then, there were added in succession, 54 ml (35 g, 0.39 mole) triethylamine and 32.9 g (0.13 mole) 2,3,4-trichlorobenzoyl chloride dissolved in 125 ml 1,2-dichloroethane. When the addition of both the amine and the benzoyl chloride had been completed, the temperature of the reaction mixture was raised to 40° C. and the mixture allowed to react for 2 hours. At the end of this time, monitoring with a high pressure liquid chromatograph indicated 84.6 area percent of the desired product, with the majority of the remainder being unreacted cyclohexanedione.

The reaction mixture was then cooled and diluted with 100 ml water. The pH, which was 9.8, was adjusted to 2.8 by addition of 3M sulfuric acid with an additional 100 ml 1,2-dichloroethane added during this step to redissolve solids which began to precipitate. The mixture was separated into aqueous and organic phases. The aqueous layer (about 200 ml) had a pH of 2.6.

The organic phase was washed with water and again phase separated (the aqueous phase had a pH of 4). The organic phase was then washed with 2 portions of 2.5N aqueous sodium hydroxide and again phase separated after each wash. The aqueous phases had pH values of 10.7 and 12.8, respectively. The organic phase was again washed with 100 ml water.

All of the aqueous phases obtained from the separation steps above were combined and acidified with 3M sulfuric acid. The pH value had been reduced to 2.1. The combined aqueous phases were kept at a low temperature in an ice bath. Solids precipitated from solution and were collected by filtration. The solids were dried to a constant weight in a vacuum oven. There was obtained 39.19 grams of the desired product, m.p. 150°–151° C. The structure of the product was confirmed by high pressure liquid chromatographic analysis and comparison with a known sample.

EXAMPLE 8

Production of 2-Propanoyl-1,3-cyclohexanedione

To a mixture of 3.0 g (0.027 mole) of 1,3-cyclohexanedione and 3.8 ml (0.027 mole) of triethylamine in 15 ml methylene chloride, there was added dropwise 2.3 ml (0.027 mole) of propionyl chloride with stirring and cooling in a room temperature water bath. After continued stirring at ambient temperature for about 4 hours, an additional 7.5 ml (0.054 mole) of triethylamine and 0.25 ml (10 mole percent with respect to enol ester) of acetone cyanohydrin were added. The mixture was stirred at ambient temperature overnight, and was then diluted with water and acidified with 6N hydrochloric acid. The phases were separated, and the aqueous phase was extracted with methylene chloride. The combined organic phases were dried over anhydrous sodium sulfate and concentrated under reduced pressure to give 4.68 g of crude product as a mixture of solid and liquid. The crude product was dissolved in methylene chloride and was extracted with 2.5N sodium hydroxide solution followed by water. The combined aqueous phases were acidified with 6N hydrochloric acid and extracted with methylene chloride. The organic extract was dried over anhydrous sodium sulfate and concentrated under reduced pressure to give 3.83 g of oily product (84% of theoretical). Structure of the product was confirmed by infrared, nuclear magnetic resonance and mass spectroscopy.

EXAMPLES 9 AND 10

These examples illustrate the production of compounds described in U.S. patent application Ser. No. 683,900 of Charles G. Carter, entitled "Certain 2-(2-Nitrobenzoyl-1,3-Cyclohexanediones", filed Dec. 20, 1984.

EXAMPLE 9

2-(2'-Nitrobenzoyl)-1,3-cyclohexanedione

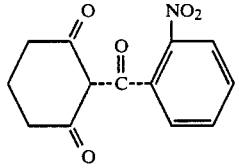

2-Nitrobenzoyl chloride (5.0 g, 0.027 mole) and cyclohexanedione (3.0 g, 0.027 mole) were dissolved in methylene chloride. Triethylamine (4.9 ml, 0.035 mole) was added dropwise and the resulting solution stirred for one hour. The solution was washed with 2N hydrochloric acid (2N HCl), water, 5% potassium carbonate solution and saturated sodium chloride solution, dried over anhydrous magnesium sulfate (MgSO4) and concentrated under vacuum. The residue was dissolved in 20 ml acetonitrile. Triethylamine (1 equivalent) and potassium cyanide (40 mole %) were added and the solution stirred for one hour at room temperature. After dilution with ether, the solution was washed with 2N HCl and extracted with 5% potassium carbonate solution. The aqueous extract was acidified and ether was added. Filtration of the resulting mixture yielded 3.2 g of the desired compound (m.p. 132°–135° C.) which was identified by nuclear magnetic resonance, infrared and mass spectroscopy.

EXAMPLE 10

2-(2'-Nitrobenzoyl)-5,5-dimethyl-1,3-cyclohexanedione

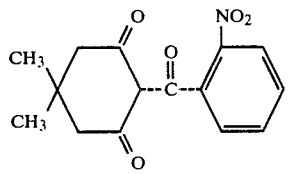

Triethylamine (3.4 ml, 0.025 mole) was added dropwise to a methylene chloride solution of 2-nitrobenzoyl chloride (3.5 g, 0.019 mole) and 5,5-dimethylcyclohexanedione (2.4 g, 0.019 mole). After stirring for one hour at room temperature an additional 3 equivalents of triethylamine and 0.4 ml acetone cyanohydrin were added. The solution was stirred for 2.5 hours, then washed with 2N HCl and extracted with 5% potassium carbonate solution. The basic extracts were acidified with 2N HCl and extracted with ether. The ether portion was washed with saturated sodium chloride solution, dried over anhydrous MgSO4 and concentrated under vacuum. The residue was recrystallized from ethyl acetate yielding 2.0 g of the desired compound (m.p. 130°–133° C.) which was identified as such by nuclear magnetic resonance, infrared and mass spectroscopy.

EXAMPLE 11

2-(2'-Cyanobenzoyl)-4,4-dimethyl-1,3-cyclohexanedione

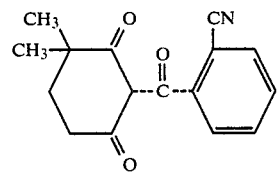

This example illustrates the production of a compound described in U.S. patent application Ser. No. 683,899, of Charles G. Carter, entitled "Certain 2-(2'-Cyanobenzoyl)-1,3-Cyclohexanediones," filed Dec. 20, 1984.

2-Cyanobenzoyl chloride (3.9 g, 0.024 mole) and 4,4-dimethyl-1,3-cyclohexanedione (3.3 g, 0.024 mole) were dissolved in 75 ml methylene chloride. Triethylamine (5.0 ml, 0.036 mole) was added dropwise and the resulting solution stirred for one and one-half hours at room temperature. The solution was washed with water, 2N HCl, 5% potassium carbonate solution (5% $K_2CO_3$) and saturated sodium chloride solution (brine), dried over anhydrous magnesium sulfate (MgSO4) and concentrated under vacuum. The residue was dissolved in 20 ml acetonitrile. Triethylamine (4.4 ml, 0.032 mole) and acetone cyanohydrin (5 drops) were added and the solution stirred for two hours. After dilution with ether, the solution was washed with 2N HCl and extracted with 5% $K_2CO_3$. The aqueous extract was acidified with concentrated hydrochloric acid and extracted with ether. The ether was washed with water and brine, dried over MgSO4 and concentrated under vacuum. The residue was purified by silica gel chromatography, yielding 1.2 g of a viscous oil which was identified as the desired compound by nuclear magnetic resonance, infrared and mass spectroscopy.

EXAMPLE 12

2-(2'-Methylthiobenzoyl)-4,4,6-trimethyl-1,3-cyclohexanedione

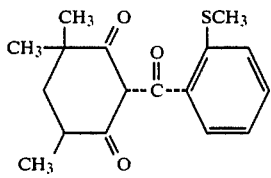

This example illustrates the production of a compound described in U.S. patent application Ser. No. 683,898, of Charles G. Carter et al., entitled "Certain 2-(2'-Substituted benzoyl)-1,3-Cyclohexanediones," filed concurrently herewith.

2-Methylthiobenzoyl chloride (7.2 g, 0.039 mole) and 4,4,6-trimethylcyclohexanedione (5.0 g, 0.039 mole) were dissolved in methylene chloride. Triethylamine (7.0 ml, 0.050 mole) was added dropwise and the resulting solution stirred for one hour at room temperature. The solution was washed with 2N HCl, 5% $K_2CO_3$ and brine, dried over $MgSO_4$ and concentrated under vacuum. The residue was dissolved in 20 ml acetonitrile. Triethylamine (2.5 equivalents) and acetone cyanohydrin (0.4 ml) were added and the solution stirred for 45 minutes at room temperature. After dilution with ether, the solution was washed with 2N HCl and extracted with 5% $K_2CO_3$. The aqueous extract was acidified with hydrochloric acid and extracted with ether. The ether was washed with brine, dried over $MgSO_4$ and concentrated under vacuum. The residue was purified by trituration with ether, yielding 5.0 g of a viscous oil which was identified as the desired compound by nuclear magnetic resonance, infrared and mass spectroscopy (ms).

EXAMPLE 13

2-(4'-Bromo-2'-trifluoromethylbenzoyl)-4,4,6-trimethyl-1,3-cyclohexanedione

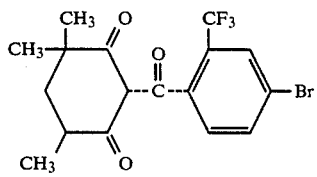

This example illustrates the production of a compound described in U.S. patent application Ser. No. 673,884, of Charles G. Carter, entitled "Certain 2-(2-Alkylbenzoyl)-1,3-Cyclohexanediones," filed Dec. 20, 1984.

4-Bromo-2-trifluoromethylbenzoyl chloride (4.3 g, 0.015 mole) and 4,4,6-trimethyl-1,3-cyclohexanedione (2.3 g, 0.015 mole) were dissolved in 100 ml methylene chloride. The solution was cooled with an ice bath and triethylamine (2.1 ml, 0.015 mole) in 10 ml methylene chloride was added dropwise. The ice bath was then removed and the resulting solution stirred for 30 minutes at room temperature. The solution was washed with 2N hydrochloric acid (2N HCl), 5% potassium carbonate solution (5% $K_2CO_3$) and saturated sodium chloride solution (brine), dried over anhydrous magnesium sulfate ($MgSO_4$) and concentrated under vacuum. The residue (5.1 g) was dissolved in 20 ml acetonitrile. Triethylamine (3.5 ml, 0.025 mole) and 0.4 ml acetone cyanohydrin were added and the solution stirred for two hours at room temperature while protected by a drying tube (calcium sulfate). After dilution with ether, the solution was washed with 2N HCl and extracted with 5% $K_2CO_3$. The aqueous extract was acidified with concentrated hydrochloric acid and extracted with ether. The ether was washed with brine, dried ($MgSO_4$) and concentrated under vacuum. The resulting oil was purified on a silica gel column (80:20:1 hexane:ethyl ethyl acetate:acetic acid—eluent), yielding 1.5 g of a viscous oil which was identified by nuclear magnetic resonance, infrared and mass spectroscopy.

EXAMPLE 14

2-(4'-Chlorobenzoyl)-5,5-dimethyl-1,3-cyclohexanedione

This example illustrates the conduct of the process using hydrogen cyanide (generated by reaction of sodium cyanide with sulfuric acid) as the cyanide source.

5,5-Dimethylcyclohexane-1,3-dione (7.01 g, 0.05 mole) acetonitrile (80 ml) and trimethylamine (21 ml, 0.15 mole) were combined in a flask and placed under a nitrogen atmosphere. A solution of 4-chlorobenzoyl chloride (6.4 ml, 0.05 mole) in acetonitrile (20 ml) was added over 15 minutes while stirring and cooling with an ambient temperature water bath. In a separate reaction flask connected by a subsurface gas inlet tube, a solution of sulfuric acid (0.25 g, 0.0025 mole) in water (10 ml) was added over 10 minutes to a solution of sodium cyanide (0.25 g, 0.005 mole) in water (30 ml) at 85° C. while stirring and slowly sweeping nitrogen through the secondary reactor and into the primary reactor. The primary reactor was then heated and stirred at 40° C. for about 2 hours whereupon the reaction was completed.

The reaction mixture was diluted with 60 ml of water and slowly acidified with 40 ml of 6N HCl with precipitation of the product. After stirring for about 5 minutes, the solid product was collected by filtration, washed with water, and dried to give 11.85 g (85.0% of theoretical yield) of off-white solids: m.p. 134°–134.5° C.

EXAMPLE 15

2-(4'-Chlorobenzoyl)-5,5-dimethyl-1,3-cyclohexanedione

This example illustrates the conduct of the process using a trilower alkyl silyl cyanide as the cyanide source.

5,5-dimethylcyclohexane-1,3-dione (7.01 g, 0.05 mole), acetonitrile (80 ml), and triethylamine (21 ml, 0.15 mole) were combined in a flask, and placed under a nitrogen atmosphere. A solution of 4-chlorobenzoyl chloride (6.4 ml, 0.05 mole) in acetonitrile (20 ml) was added over 15 inutes while stirring and cooling with an ambient temperature water bath. Trimethylsilyl cyanide (0.33 ml, 2.55 mmole) was added, and the reaction was heated and stirred at 40° C. for 3 hours whereupon the reaction was complete.

The reaction mixture was diluted with 160 ml of water and acidified with 40 ml of 6N hydrochloric acid solution with precipitation of the product. After stirring for about 10 minutes, the product was collected by filtration and was washed with water and dried to afford 13.2 g (95.0% of theoretical yield) of off-white solids: m.p. 135°–134.5° C.

EXAMPLE 16

2-(2'-Cyanobenzoyl)-1,3-cyclohexanedione

This example illustrates the conduct of the second embodiment of the process, using a stoichiometric amount of potassium cyanide and a crown ether.

In a flask were placed 1.2 g (0.005 mole) of the enol ester prepared by reaction of 1,3-cyclohexanedione with 2-cyanobenzoyl chloride, potassium cyanide (0.3 g, 0.005 mole), 18-crown-6 (0.1 g, 0.005 mole) and 10 ml acetonitrile. The mixture was stirred at room temperature for 30 minutes, then poured into 300 ml water. The pH was carefully adjusted to about 6 with concentrated hydrochloric acid; then the solution was extracted with 200 ml ethyl acetate. This in turn was extracted with 300 ml saturated aqueous solution of sodium bicarbonate. The bicarbonate extract was acidified (to pH about 3) with concentrated hydrochloric acid and extracted with 200 ml ethyl acetate. The resulting solution was dried over sodium sulfate and stripped, yielding 0.7 g (58% of theoretical yield) of the desired product, an orange-brown oil. The structure was confirmed by infrared, nuclear magnetic resonance, and mass spectroscopy.

EXAMPLE 17

2-(4'-Chlorobenzoyl)-5,5-dimethyl-1,3-cyclohexanedione

This example illustrates the conduct of the process using an alkali metal carbonate as the base.

5,5-Dimethylcyclohexane-1,3-dione (3.50 g, 0.025 mole), potassium carbonate (10 g), potassium cyanide (0.2 g), and dimethylformamide (40 ml) were combined in a flask and placed under a nitrogen atmosphere. p-Chlorobenzoyl chloride (3.5 ml, 0.025 mole) was added dropwise. The mixture was stirred at 40° C. for 3 hours and 70° C. for 2 hours.

The reaction mixture was diluted with methylene chloride and acidified with 3N hydrochloric acid solution. The organic phase was washed with water and extracted with 2.5N sodium hydroxide solution. The basic extract was acidified with 3N hydrochloric acid solution. The precipitated product was collected by filtration, washed with water, and dried to afford 5.46 g (78.0% of theoretical yield) of crude product. Analysis of the product by HPLC (high performance liquid chromatography) showed 63% by weight of 2-(4'-chlorobenzoyl)-5,5-dimethyl-1,3-cyclohexanedione. p-Chlorobenzoic acid was the only major impurity.

EXAMPLE 18

2-(2'-Nitro-4'-chlorobenzoyl)-4,4,6,6-tetramethyl-1,3,5-cyclohexanetrione

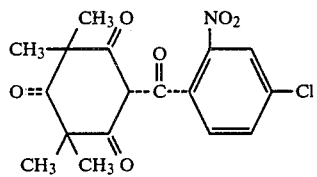

This example illustrates the production of an acylated cyclohexanetrione as described in U.S. patent application Ser. No. 872,067, of Charles G. Carter, entitled "Certain 2-Benzoyl,1,3,5-cyclohexanetriones", filed concurrently herewith.

2-Nitro-4-chlorobenzoyl chloride (2.2 g, 10 mmol) and 4,4,6,6-tetramethyl-1,3,5-cyclohexanetrione (1.8 g, 10 mmol) were dissolved in methylene chloride. Triethylamine was added and the resulting solution stirred at room temperature for 30 minutes. The solution was washed with 1 normal hydrochloric acid (1N HCl), and saturated sodium chloride (brine), dried over anhydrous magnesium sulfate (MgSO$_4$) and concentrated under vacuum. The residue was dissolved in 20 ml acetonitrile. Triethylamine (5 ml, 3.5 equivalents) and acetone cyanohydrin (0.5 g, 0.6 equivalent) were added and the mixture stirred at room temperature for 4 hours. After dilution with ether, the solution was washed with 1N HCl and extracted with 5% K$_2$CO$_3$. The basic extract was acidified with HCl and extracted with ether. The ether extract was washed with brine, dried over MgSO$_4$ and concentrated under vacuum, yielding 2.2 g of crude product. This was recrystallized from benzene to remove syncarpic acid still present. Concentration of the mother liquor under vacuum gave 1.7 g of the desired product as an oil. It was identified as such by nuclear magnetic resonance spectroscopy, infrared spectroscopy and mass spectroscopy.

EXAMPLE 19

3-(2-Nitrobenzoyl)-6-methyl-4-oxovalerolactone

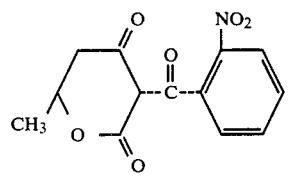

This example illustrates the production of a heterocyclic compound as described in U.S. patent application Ser. No. 871,975, of Donald R. James, William J. Michaley, Christopher Knudsen and Hsaio-Ling Chin, entitled Certain 4-Oxo-3-benzoylvalerolactones and Thiolactones", filed concurrently herewith.

6-Methyl-4-oxovalerolactone (2.6 g, 20 mmol) and 2-nitrobenzoylchloride (3.8 g, 20 mmol) were dissolved in 30 ml methylene chloride and stirred at room temperature. Triethylamine (2.2 g, 20 mmol) in 20 ml methylene chloride was added dropwise, and the resulting mixture was stirred for 2 hours. The reaction mixture was then poured into 1N HCl and extracted with additional methylene chloride. The organic layer was then washed with 5% K$_2$CO$_3$, brine, then dried with MgSO$_4$ and evaporated to yield an oil (4.2 g, 76%) which was used without further purification.

Two and sixty-seven one-hundredths grams (10 mmol) of the prepared enol ester was dissolved in 50 ml acetonitrile and stirred at room temperature. Triethylamine (2.0 g, 20 mmol) and acetone cyanohydrin (0.1 g, 1 mmol) were added all at once, and the resulting mixture stirred for 5 hours. The solvent was evaporated and the resulting oil dissolved in ether. The organic liquid was then washed with 1N HCl, brine, dried with MgSO$_4$ and evaporated to yield an oil which crystallized on standing (2.3 g, 86%, m.p. 84°–89° C., which was indentified as the desired compound by nuclear magnetic resonance spectroscopy, infrared spectroscopy and mass spectroscopy.

EXAMPLE 20

5-(2,4-Dichlorobenzoyl)-1,3-dimethyl-barbituric acid

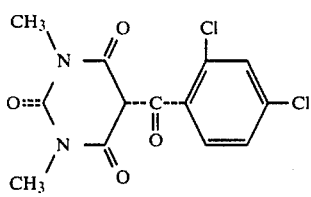

This example illustrates the production of a compound having two hetero atoms in the dicarbonyl portion of the molecule, as described in U.S. patent application Ser. No. 872,068, of David L. Lee and Charles G. Carter, entitled "Certain 5-(2-Substituted Benzoyl)-Barbituric Acids", filed concurrently herewith.

1,3-Dimethylbarbituric acid (15.6 g, 0.1 mole), 2,4-dichlorobenzoyl chloride (20.9 g, 0.1 mole) and zinc cyanide (12.9 g, 0.11 mole) were combined in acetonitrile (175 ml). Triethylamine (10.1 g, 0.12 mole) was slowly added with cooling. The reaction mixture was then heated at reflux for one hour. After cooling, the reaction mixture was poured into 2N hydrochloric acid. The resulting product precipitate was filtered and washed with ether to afford 26.4 grams of the desired product, m.p. 123°-127° C. (80.2% yield). The structure was confirmed by instrumental analysis.

EXAMPLE 21

4-(2,4-Dichlorobenzoyl)-2H-thiopyran-3,5(4H,6H)-dione

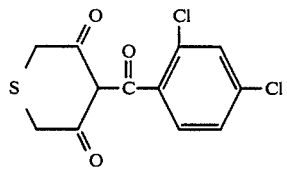

This example illustrates the production of a compound having a sulfur-containing heterocyclic ring, as described in U.S. patent application Ser. No. 872,080, of Jeffrey K. Curtis and Charles G. Carter, entitled "Certain Substituted 4-Benzoyl-3,5-Dioxotetrahydropyrans and Thiopyrans", filed concurrently herewith.

Triethylamine (3 g, 30 mmol) was added dropwise to a solution of 2,4-dichlorobenzoyl cyanide (3 g, 15 mmol) and 2H-thiopyran-3,5-(4H,6H)-dione (2 g, 15 mmol) in acetonitrile and stirred at room temperature for thirty minutes. Diethyl ether was added and the solution was washed with dilute hydrochloric acid and brine, dried over anhydrous magnesium sulfate and concentrated under vacuum. The residue was purified by column chromatography to yield 2.0 g of a viscous oil. It was identified as the desired product by nuclear magnetic spectroscopy, infrared spectroscopy and mass spectroscopy.

EXAMPLE 22

3-(2-Nitro-4-chlorobenzoyl)-1,5-dimethyl-4-oxovalerolactam

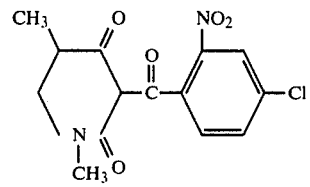

This examples illustrates the production of an oxolactam as described in U.S. patent application Ser. No. 871,973 now abandoned, CIP 021,811 filed 3/13/87, of Jeffrey K. Curtis, entitled "Certain 1-Benzoyl-4-oxolactams", filed concurrently herewith.

2-Nitro-4-chlorobenzoyl chloride (3.7 g, 17 mmol) and 1,5-dimethyl-4-oxovalerolactam (3.0 g, 17 mmol) were dissolved in 150 ml methylene chloride. Triethylamine (1.7 g, 17 mmol) was added and the resulting solution was stirred at room temperature for fifteen minutes. The solution was washed with dilute hydrochloric acid, 5% potassium carbonate and saturated sodium chloride, dried over magnesium sulfate and concentrated under vacuum. The residue was dissolved in 20 ml of acetonitrile. Triethylamine (1.7 g, 17 mmol) potassium cyanide (0.1 g, 1.5 mmol) and 18-crown-6 (0.1 g, 0.4 mmol) were added and the mixture stirred at room temperature for 20 minutes. After dilution with ether, the solution was washed with dilute hydrochloric acid and extracted with 5% potassium carbonate. The basic extract was acidified with hydrochloric acid and extracted with chloroform. The chloroform extract was washed with 10% cupric acetate, water, saturated sodium bicarboante, and 2N hydrochloride acid. The chloroform layer was washed with water, dried over MgSO4 and evaporated to yield a yellow solid (2.0 g, m.p. 119°-120° C.) which was identified as the desired compound by nuclear magnetic resonance spectroscopy, infrared spectroscopy and mass spectroscopy.

What is claimed is:

1. A process for producing an acylated cyclical 1,3-dicarbonyl compound by rearrangement of the corresponding enol ester in which the rearrangement is conducted in the presence of a cyanide source which is an alkali metal cyanide, a cyanohydrin of a methyl alkyl ketone having from 1 to 4 carbon atoms in the alkyl group, benzaldehyde cyanohydrin, cyclohexanone cyanohydrin, a cyanohydrin of a $C_2$–$C_5$ aliphatic aldehyde, lactonitrile, a lower alkyl silyl cyanide, potassium ferricyanide, or hydrogen cyanide.

2. A process according to claim 1 in which the rearrangement is conducted in the presence of either
   (a) a catalytic amount of a cyanide source and a molar excess, with respect to the enol ester, of a moderate base; or
   (b) a stoichiometric amount, with respect to the enol ester, of potassium cyanide or lithium cyanide, and a catalytic amount of a cyclical crown ether or an acyclic analog thereof.

3. A process according to claim 2 in which the rearrangement is conducted in the presence of a cyanide source, and a molar excess, with respect to the enol ester, of a moderate base.

4. A process according to claim 3 in which the cyanide source is an alkali metal cyanide, cyanohydrin of a methyl alkyl ketone having from 1 to 4 carbon atoms in the alkyl group, benzaldehyde cyanohydrin, cyclohexanone cyanohydrin, a cyanohydrin of a $C_2$-$C_5$ aliphatic alkehyde, lactonitrile, a lower alkyl silyl cyanide, potassium ferricyanide, or hydrogen cyanide.

5. A process according to claim 4 in which the cyanide source is hydrogen cyanide.

6. A process according to claim 4 in which the cyanide source is sodium cyanide.

7. A process according to claim 4 in which the cyanide source is potassium cyanide.

8. A process according to claim 4 in which the cyanide source is a ketone or aldehyde cyanohydrin.

9. A process according to claim 8 in which the cyanide source is acetone cyanohydrin.

10. A process according to claim 3 in which the cyanide source is trimethyl silyl cyanide.

11. A process according to claim 3 in which the cyanide source is used in an amount of up to about 50 mole percent, based on the enol ester.

12. A process according to claim 11 in which the cyanide source is used in an amount of from about 1 to about 10 mole percent, based on the enol ester.

13. A process according to claim 3 in which the moderate base is a trialkylamine, an alkali metal carbonate or an alkali metal phosphate.

14. A process according to claim 13 in which the base is a trialkylamine having from 1 to 6 carbon atoms in each alkyl group.

15. A process according to claim 14 in which the base is triethylamine.

16. A process according to claim 13 in which the base is an alkali metal carbonate.

17. A process according to claim 16 in which the base is potassium carbonate.

18. A process according to claim 3 in which the base is used in an amount of from about 1 to about 4 moles per mole of enol ester.

19. A process according to claim 3 in which the temperature is from about 0° C. to about 100° C.

20. A process according to claim 2 in which the rearragement is conducted in the presence of a stoichiometric amount, with respect to the enol ester, of potassium cyanide or lithium cyanide and a catalytic amount of a cyclical crown ether or an acyclic analog thereof.

21. A process according to claim 20 in which the rearrangement is conducted in the presence of a stoichiometric excess, with respect to the enol ester, of potassium cyanide, and of a catalytic amount of 18-crown-6.

22. A process according to claim 1 in which the acylated dicarbonyl compound is a derivative of a 1,3-cyclohexanedione.

23. A process according to claim 22 in which the acylated dicarbonyl compound is substituted benzoyl derivative of a 1,3-cyclohexanedione.

24. A process according to claim 23 in which the acylated dicarbonyl compound has the formula

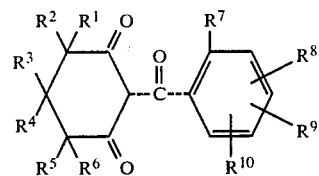

in which
$R^1$, $R^2$, $R^3$, $R^4$, $R^5$ and $R^6$ are independently hydrogen or $C_1$-$C_4$ alkyl (preferably $C_1$-$C_4$ alkyl) or $R^1$ or $R^3$ is

in which $R_a$ is $C_1$-$C_4$ alkyl, phenyl, optionally substituted by from 2 to 5 methyl groups;
or in which $R^1$ and $R^2$ or $R^3$ and $R^4$, taken together are $C_2$-$C_5$ alkylene;
$R^7$ is halogen; cyano; $C_1$-$C_4$ alkyl; $C_1$-$C_4$ haloalkyl; $R_kS-$ in which $R_k$ is $C_1$-$C_4$ alkyl, $C_1$-$C_4$ alkoxy or nitro;
$R^8$, $R^9$ and $R^{10}$ independently are hydrogen; halogen; $C_1$—$C_1$-$C_4$—$C_4$ alkyl; alkoxy, trifluoromethoxy; cyano; nitro; $C_1$-$C_4$ haloalkyl; $C_1$-$C_4$ alkylthio; phenoxy; or substituted phenoxy in which the substituent is halogen or halomethyl or both;
$R_bS(O)n$ in which n is 0, 1 or 2; and $R_b$ is $C_1$-$C_4$ alkyl, $C_1$-$C_4$ haloalkyl, phenyl or benzyl,

in which $R_c$ is $C_1$-$C_4$ alkyl,
$-NR_dR_e$ in which $R_d$ and $R_e$ independently are hydrogen or $C_1$-$C_4$ alkyl;
$R_fC(O)-$ in which $R_f$ is hydrogen, $C_1$-$C_4$ alkyl, $C_1$-$C_4$ haloalkyl or $C_1$-$C_4$ alkoxy;
$SO_2NR_gR_h$ in which $R_g$ and $R_h$ independently are hydrogen or $C_1$-$C_4$ alkyl;
or $R^8$ and $R^9$ taken together form a ring structure with two adjacent carbon atoms of the phenyl ring to which they are attached.

25. A process according to claim 1 in which the acylated dicarbonyl compound is a derivative of a 1,3-cyclopentanedione.

26. A process according to claim 1 in which the acylated dicarbonyl compound is a derivative of a 1,3,5-cyclohexanetrione.

27. A process according to claim 1 in which the acylated dicarbonyl compound is a derivative of a 1,3-dicarbonyl heterocyclic compound having a total of 5-6 atoms in the ring, including from 1 to 2 atoms selected from the group consisting of nitrogen, oxygen and sulfur.

28. A process according to claim 1 in which the enol ester is produced by reaction of a 1,3-dicarbonyl compound with an acyl halide.

29. A process according to claim 28 in which the rearrangement of the enol ester is performed without isolation of said ester from the product resulting from the reaction of the dicarbonyl compound with the acyl halide.

30. A process for producing a benzoylated cyclical 1,3-dicarbonyl compound by rearrangement of the corresponding enol ester in which the rearrangement is conducted in the presence of a cyanide source.

31. A process according to claim 30 in which the acylated dicarbonyl compound is a derivative of a 1,3-cyclohexanedione.

32. A process according to claim 30 in which the acylated dicarbonyl compound has the formula

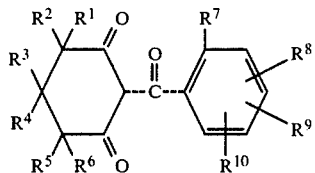

in which
$R^1$, $R^2$, $R^3$, $R^4$, $R^5$ and $R^6$ are independently hydrogen or $C_1-C_6$ alkyl or
$R^1$ or $R^3$ is

in which $R^a$ is $C_1-C_4$ alkyl, phenyl, optionally substituted by from 2 to 5 methyl groups;
or in which $R^1$ and $R^2$ or $R^3$ and $R^4$, taken together are $C_2-C_5$ alkylene;

$R^7$ is halogen; cyano; $C_1-C_4$ alkyl; $C_1-C_4$ haloalkyl; $R_kS-$ in which $R_k$ is $C_1-C_4$ alkyl, $C_1-C_4$ alkoxy or nitro;

$R^8$, $R^9$ and $R^{10}$ independently are hydrogen; halogen; $C_1-C_4$ alkyl; $C_1-C_4$ alkoxy, trifluoromethoxy; cyano; nitro; $C_1-C_4$ haloalkyl; $C_1-C_4$ alkylthio; phenoxy; or substituted phenoxy in which the substituent is halogen or halomethyl or both;

$R_bS(O)n$ in which n is 0, 1 or 2; and $R_b$ is $C_1-C_4$ alkyl, $C_1-C_4$ haloalkyl, phenyl or benzyl,

in which $R_c$ is $C_1-C_4$ alkyl, $-NR_dR_e$ in which $R_d$ and $R_e$ independently are hydrogen or $C_1-C_4$ alkyl;

$R_fC(O)-$ in which $R_f$ is hydrogen, $C_1-C_4$ alkyl, $C_1-C_4$ haloalkyl or $C_1-C_4$ alkoxy;

$SO_2NR_gR_h$ in which $R_g$ and $R_h$ independently are hydrogen or $C_1-C_4$ alkyl;

or $R^8$ and $R^9$ taken together form a ring structure with two adjacent carbon atoms of the phenyl ring to which they are attached.

33. A process according to claim 30 in which the acylated dicarbonyl compound is a derivative of a 1,3,5-cyclohexanetrione.

34. A process according to claim 33 in which the acylated dicarbonyl compound has the formula

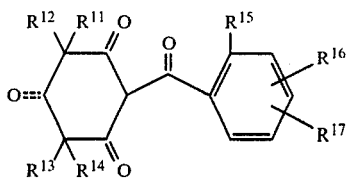

wherein
$R^{11}$ is hydrogen or $C_1-C_4$ alkyl;
$R^{12}$ is hydrogen or $C_1-C_4$ alkyl;
$R^{11}$ and $R^{12}$ together are $C_2-C_5$ alkylene;
$R^{13}$ is hydrogen or $C_1-C_4$ alkyl;
$R_{14}$ is hydrogen or $C_1-C_4$ alkyl;
$R^{13}$ and $R^{14}$ together are $C_2-C_5$ alkylene;
$R^{15}$ is hydrogen; halogen; $C_1-C_2$ alkyl; $C_1-C_2$ alkoxy; nitro; cyano; $C_1-C_2$ haloalkyl or $R^mS-$ wherein $R^m$ is $C_1-C_2$ alkyl, trifluoromethyl or difluoromethyl; trifluoromethoxy or difluoromethoxy; and
$R^{16}$ and $R^{17}$ independently are (1) hydrogen; (2) halogen; (3) $C_1-C_4$alkyl; (4) $C_1-C_4$ alkoxy; (5) trifluoromethoxy; (6) cyano; (7) nitro; (8) $C_1-C_4$ haloalkyl; (9) $R^bSO_n-$ wherein n is the integer 0, 1 or 2; and
$R^b$ is
  (a) $C_1-C_4$ alkyl;
  (b) $C_1-C_4$ alkyl substituted with halogen or cyano;
  (c) phenyl; or
  (d) benzyl;
(10) $-NR^dR^e$ wherein
  $R^d$ and $R^e$ independently are hydrogen or $C_1-C_4$ alkyl;
(11) $R^fC(O)-$ wherein $R^f$ is $C_1-C_4$ alkyl or $C_1-C_4$ alkoxy;
(12) $-SO_2NR^dR^e$; or
(13) $-N(R^d)C(O)R^e$.

35. A process according to claim 30 in which the acylated dicarbonyl compound is a derivative of a 1,3-dicarbonyl heterocyclic compound having a total of 5-6 atoms in the ring, including 1-2 atoms selected from the group consisting of nitrogen, oxygen and sulfur.

36. A process according to claim 35 in which the acylated dicarbonyl compound is a substituted benzoylated 1,3-dicarbonyl heterocyclic compound having the formula

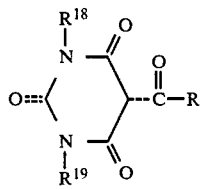

in which $R^{18}$ and $R^{19}$ are hydrogen or $C_1-C_4$ alkyl;

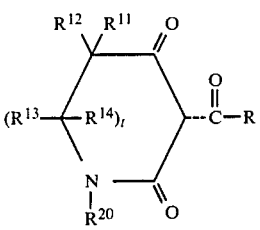

in which $R^{11}$–$R^{14}$ and $R^{20}$ are independently hydrogen or $C_1$–$C_4$ alkyl or $R^{11}$ and $R^{12}$ together are $C_2$–$C_5$ alkylene; and t is 0 or 1;

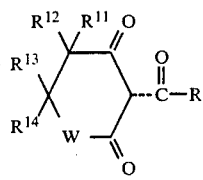

in which $R^{11}$–$R^{14}$ are independently hydrogen or $C_1$–$C_4$ alkyl; or $R^{11}$ and $R^{12}$ together are $C_2$–$C_5$ alkylene, or $R^{13}$ and $R^{14}$ are $C_2$–$C_5$ alkylene or $R^{13}$ and $R^{14}$ together form a bond and W is oxygen or sulfur; or

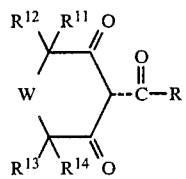

in which $R^{11}$–$R^{14}$ are independently hydrogen or $C_1$–$C_4$ alkyl; or $R^{11}$ and $R^{12}$ together are $C_2$–$C_5$ alkylene; or $R^{13}$ and $R^{14}$ together are $C_2$–$C_5$ alkylene; and W is oxygen or sulfur; and R is

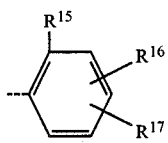

wherein
  $R^{15}$ is hydrogen; halogen; $C_1$–$C_2$ alkyl; $C_1$–$C_2$ alkoxy; nitro; cyano; $C_1$–$C_2$ haloalkyl; $R^{m}$S— wherein $R^{m}$ is $C_1$–$C_2$ alkyl, trifluoromethyl or difluoromethyl; trifluoromethoxy or difluoromethoxy;
  $R^{16}$ and $R^{17}$ independently are (1) hydrogen; (2) halogen; (3) $C_1$–$C_4$ alkyl; (4) $C_1$–$C_4$ alkoxy; (5) trifluoromethoxy; (6) cyano; (7) nitro; (8) $C_1$–$C_4$ haloalkyl; (9) $R^{b}SO_n$— wherein n is the integer 0, 1 and 2; and
  $R^{b}$ is
    (a) $C_1$–$C_4$ alkyl;
    (b) $C_1$–$C_4$ alkyl substituted with halogen or cyano;
    (c) phenyl; or
    (d) benzyl;
  (10) —$NR^{d}R^{e}$ wherein
    $R^{d}$ and $R^{e}$ independently are hydrogen or $C_1$–$C_4$ alkyl;
  (11) $R^{f}C(O)$— wherein $R^{f}$ is $C_1$–$C_4$ alkyl or $C_1$–$C_4$ alkoxy;
  (12) —$SO_2NR^{d}R^{e}$; or
  (13) —$N(R^{d})C(O)R^{e}$.

37. A process according to claim 30 in which the rearrangement is conducted in the presence of either.
  (a) a catalytic amount of a cyanide source and a molar excess, with respect to the enol ester, of a moderate base; or
  (b) a stoichiometric amount, with respect to the enol ester, of potassium cyanide of lithium cyanide, and a catalytic amount of a cyclical crown ether or an acyclic analog thereof.

38. A process according to claim 37 in which the rearrangement is conducted in the presence of a cyanide source, and a molar excess, with respect to the enol ester, of a moderate base.

39. A process according to claim 38 in which the cyanide source is zinc cyanide, an alkali metal cyanide, a cyanohydrin of a methylalkyl ketone having from 1 to 4 carbon atoms in the alkyl group, benzaldehyde cyanohydrin, cyclohexanone cyanohydrin, a cyanohydrin of a $C_2$–$C_5$ aliphatic aldehyde, lactonitrile, a lower alkyl silyl cyanide, potassium ferricyanide, or hydrogen cyanide.

40. A compound having the formula

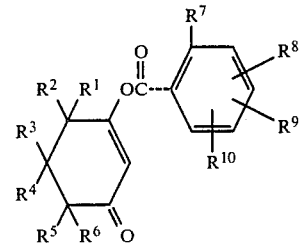

in which
  $R^1$, $R^2$, $R^3$, $R^4$, $R^5$ and $R^6$ are independently hydrogen or $C_1$–$C_4$ alkyl or
  $R^1$ or $R^3$ is

in which $R_a$ is $C_1$–$C_4$ alkyl; phenyl, optionally substituted by from 2 to 5 methyl groups;
  or in which $R^1$ and $R^2$, or $R^3$ and $R^4$, taken together are $C_2$–$C_5$ alkylene;
  $R^7$ is halogen;
  $R^8$, $R^9$ and $R^{10}$ independently are hydrogen; alkyl; $C_1$–$C_4$ alkoxy, trifluoromethoxy; cyano; nitro; $C_1$–$C_4$ haloalkyl; $C_1$–$C_4$ alkylthio; phenoxy; or substituted phenoxy in which the substituent is halogen or halomethyl or both;
  $R_bS(O)_n$ in which n is 0, 1 or 2; and $R_b$ is $C_1$–$C_4$ alkyl, $C_1$–$C_4$ haloalkyl, phenyl or benzyl,

in which $R_c$ is $C_1$–$C_4$ alkyl,
  —$NR_dR_e$ in which $R_d$ and $R_e$ independently are hydrogen or $C_1$–$C_4$ alkyl;

$R_fC(O)$— in which $R_f$ is hydrogen, $C_1$-$C_4$ alkyl, $C_1$-$C_4$ haloalkyl or $C_1$-$C_4$ alkoxy;

$SO_2NR_gR_h$ in which $R_g$ and $R_h$ independently are hydrogen or $C_1$-$C_4$ alkyl;

or $R^8$ and $R^9$ taken together form a ring structure with two adjacent carbon atoms of the phenyl ring to which they are attached.

41. A compound according to claim 40 in which $R^1$, $R^2$, $R^5$ and $R^6$ are hydrogen; $R^3$ and $R^4$ are independently hydrogen or $C_1$-$C_4$ alkyl; or $R^3$ is

in which $R_a$ is $C_1$-$C_4$ alkyl.

42. A compound according to claim 40 in which $R^1$, $R^2$, $R^3$, $R^4$, $R^5$ and $R^6$ are all hydrogen.

43. A compound according to claim 42 in which $R^7$ is chloro.

44. A compound according to claim 43 in which $R^8$ is 3-chloro, $R^9$ is 4-chloro and $R^{10}$ is hydrogen.

45. A compound according to claim 43 in which $R^8$ is hydrogen, $R^9$ is 4-methylsulfonyl and $R^{10}$ is hydrogen.

46. A compound according to claim 43 in which $R^8$ is 3-ethoxy, $R^9$ is 4-ethylsulfonyl and $R^{10}$ is hydrogen.

47. A compound according to claim 43 in which $R^8$ is 3-methoxy, $R^9$ is 4-ethylthio and $R^{10}$ is hydrogen.

48. A compound according to claim 43 in which $R^8$ is 3-(n-butoxy), $R^9$ is 4-ethylsulfonyl and $R^{10}$ is hydrogen.

49. A compound according to claim 43 in which $R^8$ is 3-methylcarbamyl, $R^9$ is 4-chloro and $R^{10}$ is hydrogen.

* * * * *

UNITED STATES PATENT AND TRADEMARK OFFICE
CERTIFICATE OF CORRECTION

PATENT NO. : 4,695,673
DATED : September 22, 1987
INVENTOR(S) : James B. Heather et al.

It is certified that error appears in the above-identified patent and that said Letters Patent is hereby corrected as shown below:

In Column 9, at line 59, the number "811,975" should read --- 871,975 ---.

In Claim 37, column 28, line 11, should read as follows--- ester, of potassium cyanide or lithium cyanide, and ---

In Claim 40, the sixth line after the second formula should read as follows: --- $R^8$, $R^9$ and $R^{10}$ independently are hydrogen or halogen; alkyl; ---

Signed and Sealed this

Ninth Day of January, 1990

*Attest:*

JEFFREY M. SAMUELS

*Attesting Officer*    *Acting Commissioner of Patents and Trademarks*